US00PP36693P2

(12) United States Plant Patent
Lee

(10) Patent No.: US PP36,693 P2
(45) Date of Patent: May 20, 2025

(54) ***RHODODENDRON* PLANT NAMED 'ROBLEZO'**

(50) Latin Name: ***Rhododendron* hybrid**
Varietal Denomination: ROBLEZO

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/935,732

(22) Filed: Nov. 4, 2024

(51) Int. Cl.
*A01H 5/00* (2018.01)
*A01H 6/36* (2018.01)

(52) U.S. Cl.
USPC ..... Plt./240

(58) Field of Classification Search
USPC ..... Plt./238, 240
See application file for complete search history.

(56) References Cited

U.S. PATENT DOCUMENTS

PP28,279 P3 * 8/2017 Lee ..... A01H 6/364
Plt./240

* cited by examiner

*Primary Examiner* — Susan McCormick Ewoldt
(74) *Attorney, Agent, or Firm* — Cassandra Bright

(57) ABSTRACT

A new and distinct cultivar of *Rhododendron* plant named 'ROBLEZO' is disclosed, characterized by unique very dark red-purple flowers with a main color of 59A. Plants bloom intermittently from early Spring until Fall. Plants have a strong root system, superior landscape qualities and are tolerant of pests. The new cultivar is a *Rhododendron*, suitable for ornamental garden purposes.

2 Drawing Sheets

Latin name of the genus and species: *Rhododendron* hybrid.

Variety denomination: 'ROBLEZO'.

BACKGROUND OF THE INVENTION

The new cultivar is a product of a planned breeding program by the inventor to develop new *Rhododendron* varieties with dark flower color, repeat blooming, all-around sturdiness, pest resistance and variable environmental adaptability. The seed and pollen parents were among unnamed, unpatented Azalea proprietary seedlings selected for the previously mentioned desired traits. The open field hand-pollination resulting in the new cultivar was made during 2012 at a nursery in Independence, Louisiana.

*Rhododendron* 'ROBLEZO' was found and selected in 2016 at the same nursery in Independence, Louisiana. The first asexual propagation occurred in the Fall of 2016 by semi-hardwood cuttings at the same nursery. 'ROBLEZO' has been found to retain its distinctive characteristics through successive asexual propagations over multiple generations.

SUMMARY OF THE INVENTION

The cultivar 'ROBLEZO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROBLEZO'. These characteristics in combination distinguish 'ROBLEZO' as a new and distinct *Rhododendron* cultivar:

1. Single, self-cleaning flowers with very dark red-purple coloring.
2. Repeat blooming in spring, summer and fall.
3. Superior landscape qualities; tolerant to environmental and climatic conditions.
4. Tolerant to pests.
5. Strong root system.

COMPARISON TO PARENT VARIETIES

Parent comparisons are unavailable.

COMMERCIAL COMPARISON

'ROBLEZO' can be compared to the commercial variety *Rhododendron* 'ROBLEZN', currently pending with application Ser. No. 18/935,725. Plants of the new cultivar 'ROBLEZO' are similar to plants of 'ROBLEZN' in most horticultural characteristics. Plants of the new cultivar 'ROBLEZO', however, differ in the following:

1. Mature upper petal color of 'ROBLEZO' is Red-Purple 59A with an overall sheet of 59C. Lower central section is irregularly dotted Greyed-Purple 187A. Overall sheen near 59C. Mature upper petal color of 'ROBLEZN' is Red-Purple 71A with an overall flush of N74B. Central petal section is irregularly dotted Greyed-Purple N186D.
2. Young branches of 'ROBLEZO' are colored Yellow-Green 152B; young branches of 'ROBLEZN' are colored Greyed-Orange 165B.
3. Flowers of 'ROBLEZO' are 6 cm long and 8 cm in diameter (on average); flowers of 'ROBLEZN' are 5 cm long and 8.5 cm in diameter (on average).

BRIEF DESCRIPTION OF THE PHOTOGRAPHS

'ROBLEZO' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describes the new hybrid *Rhododendron.*

DETAILED BOTANICAL DESCRIPTION

Figure 1:
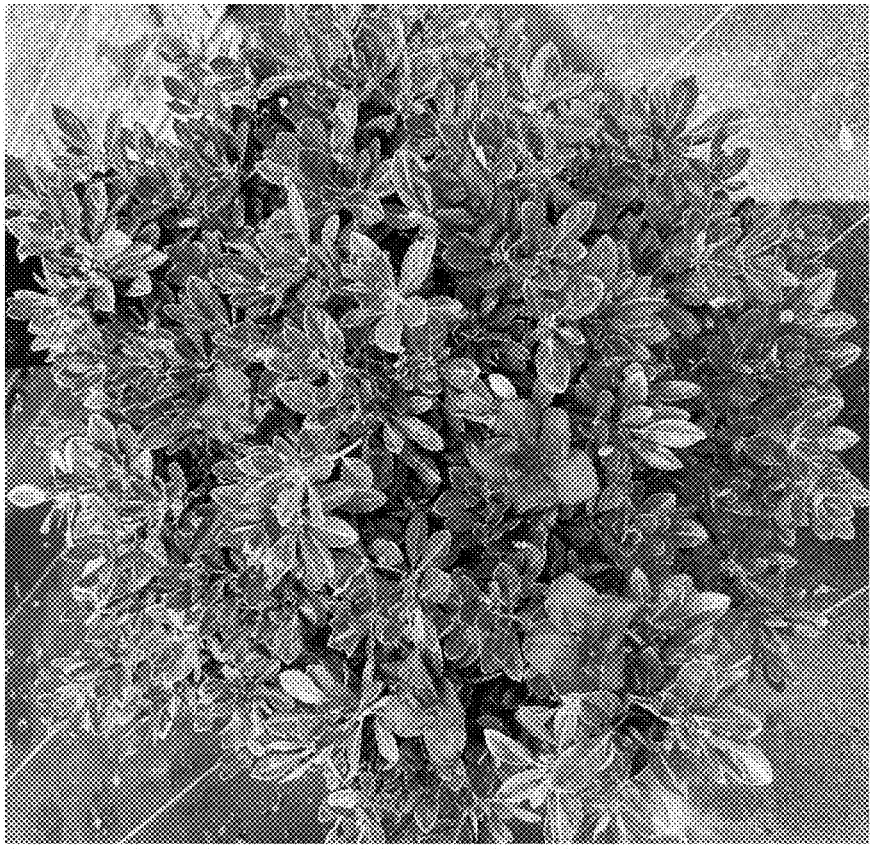
FIG. 1 depicts a 2.5-year-old plant in a 5-gallon container, photographed during September in Loxley, AL.
Figure 2:
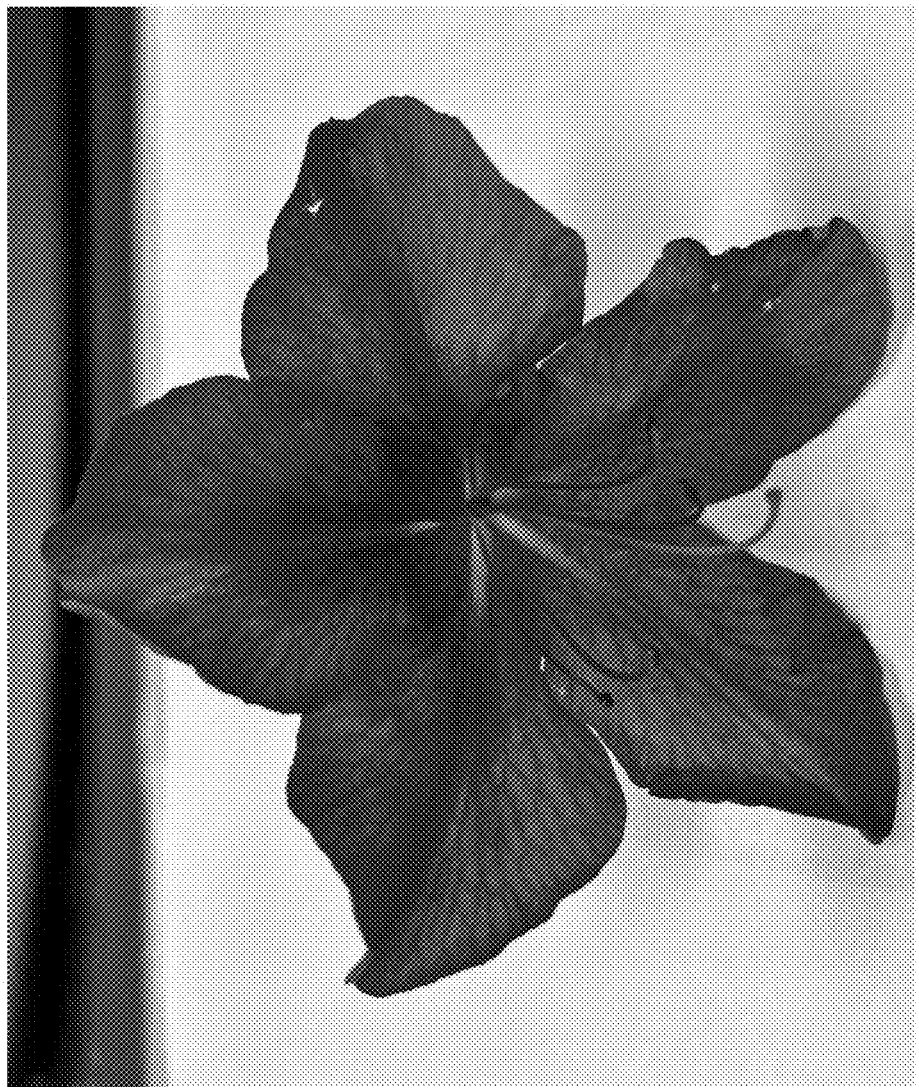
FIG. 2 is a close-up photograph of a single flower of 'ROBLEZO'.

The following is a detailed description of the botanical characteristics of the new and distinct *Rhododendron* 'ROBLEZO'. The detailed description was taken of a 1-year-old 1-gallon container plant grown in Loxley, AL in 2024. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'ROBLEZO'.

ROOTS

Typical method: Semi-hardwood cuttings.

Root description: Fine, fibrous young roots, well branched. Colored near RHS Grey-Brown 199A.

PLANT

Plant type: Flowering shrub.

Growth habit: Upright.

Height: Approximately 35 cm to top of foliar and flowering plane.

Width: Approximately 35 cm.

Growth rate: Moderate.

Vigor: Moderate.

Branching characteristics: Moderately well-branched, average 4 to 5 primary branches from the center of the plant. Branches occur at approximately 35° to 60° angles.

Length of primary branches: Average range 10 to 32 cm.

Diameter of primary branches: Average range 5 mm to 8 mm.

Primary branch strength: Very strong, difficult to break.

Primary branch color:

- *Young branches.*—Near RHS Yellow-Green 152B covered in Greyed-Orange 172A.
- *Woody branches.*—Near RHS Greyed-Purple 183A streaked Grey-Green 197A.

Primary branch texture:

- *Immature growth.*—Hirsute.
- *Older growth.*—Slightly scaly.

Lateral branches:

Number of lateral branches: Approximately 2 to 4 per primary branch.

Length of lateral branches: Average 8 cm to 16 cm.

Diameter of lateral branches: Average 4 mm.

Lateral branch strength: Very strong, flexible.

Lateral branch color: Immature branches near RHS Greyed-Purple 183A, lightly flushed Greyed-Purple 185A.

Lateral branch texture: Lightly scaly.

Internode length: Average range 3 to 4 cm.

FOLIAGE

Leaf:

- *Type.*—Simple.
- *Arrangement.*—Alternate.
- *Length.*—Approximately 6 cm.
- *Width.*—Approximately 2 cm.
- *Shape.*—Obovate.
- *Apex.*—Muconate.
- *Base.*—Attenuate.
- *Attachment.*—Stalked.
- *Margin.*—Entire.
- *Texture of top surface.*—Rough.
- *Texture of bottom surface.*—Rough.
- *Appearance of top surface.*—Glossy.
- *Appearance of bottom surface.*—Matte.
- *Color.*—Young foliage upper side: Near RHS Green 139A. Young foliage under side: Near RHS Green 137B. Mature foliage upper side: Near RHS Green 139A. Mature foliage under side: Near RHS Green 137C.

Venation:

- *Type.*—Pinnate.
- *Venation color upper side.*—Near RHS Yellow-Green N144D.
- *Venation color under side.*—Near RHS Yellow-Green N144A.

Petiole:

- *Length.*—About 13 mm.
- *Diameter.*—About 2 mm.
- *Color.*—Upper Surface: Near RHS Yellow-Green N144D. Lower Surface: Near RHS Yellow-Green N144A.
- *Texture of top surface.*—Rough.
- *Texture of bottom surface.*—Rough.

FLOWER

Natural flowering season: Intermittently from early Spring through Fall.

Arrangement: Axillary clusters of single open funnel shaped individual flowers. Typically 5 flowers per cluster.

Inflorescence:

- *Height.*—Average 8 cm.
- *Diameter.*—Average 13 cm.

Peduncle:

- *Length.*—Average 1 cm.
- *Diameter.*—4 mm.
- *Color.*—Near RHS Greyed-Purple 183A.
- *Texture.*—Rough.
- *Aspect.*—Straight. Angle of attachment, approximately 15° angle from stem.

Pedicel:

- *Length.*—Average 1.1 to 1.4 cm.
- *Diameter.*—10 mm.
- *Color.*—Near RHS Yellow-Green 145D, flushed Red-Purple 71C.
- *Texture.*—Densely pubescent.
- *Aspect.*—Straight. Approximately 45° angle from stem.

Flowers:

- *Length.*—Average 6 cm.
- *Diameter.*—Average 8 cm.

*Aspect*.—Outward facing.
*Persistence*.—Self-cleaning.
*Fragrance*.—None detected.

Tube:
*Length*.—Average 15 mm.
*Width a widest point*.—Approximately 2 cm.
*Width and narrowest point*.—Approximately 9 mm.

Petals:
*Quantity*.—5.
*Unfused petal segments*.—Length: Approximately 3.2 cm. Width: Approximately 3.2 cm.
*Apex*.—Blunt, rounded with shallow (0.05 mm), irregular lobes or notches.
*Shape*.—Unfused portion, obovate.
*Margin*.—Entire. Slightly ruffled.
*Arrangement*.—Slightly to moderately overlapping, bilateral symmetry dissecting bottom petal. Petals fused approximately ⅓ fused from base.
*Texture*.—Smooth, all surfaces.
*Color*.—Upper surface at first opening: RHS Red-Purple 59A. Lower central section irregularly dotted Greyed-Purple 187A. Under surface at first opening: RHS Red-Purple 59B. Inner surface at maturity: RHS Red-Purple 59A. Lower central section irregularly dotted Greyed-Purple 187A. Overall sheen near 59C. Outer surface at maturity: RHS Red-Purple 59B. Upper surface at fading: RHS Red-Purple 59A, margins Greyed-Purple N186A. Under surface at fading: RHS Red-Purple 59A, margins Greyed-Purple N186A.

Bud:
*Shape*.—Elliptic.
*Length*.—2.7 cm.
*Diameter*.—1.1 cm.
*Color*.—Near RHS Red-Purple 59A.

Sepals:
*Quantity per flower*.—5.
*Shape*.—Narrow deltate.
*Length*.—9 mm.
*Width*.—3 mm.
*Apex*.—Acute.
*Base*.—Fused.
*Margin*.—Entire.
*Texture*.—Highly pubescent.
*Color*.—Inner Surface: Near RHS Yellow-Green 145B. Outer Surface: Near RHS Yellow-Green 145C, flushed Red-Purple 59B.

REPRODUCTIVE ORGANS

Stamens:
*Number*.—6.
*Length*.—4.5 cm.
*Filament color*.—RHS Red-Purple 59C.
*Protrusion*.—Slightly protruding.
*Anthers*.—Length: Approximately 3 mm. Color: Near RHS Red-Purple 59A. Pollen: Not observed.

Pistil:
*Number*.—1.
*Length*.—5 cm.
*Style*.—Length: Average 4.5 cm. Color: Lower half near RHS Red-Purple 62C; upper half near Red-Purple 57A.
*Stigma*.—Shape: Globular. Color: Near RHS Red-Purple N57A.
*Ovary*.—Length: 5 mm. Diameter: Approximately 5 mm. Texture: Sericeous. Color: Near RHS Yellow-Green 144C.

OTHER CHARACTERISTICS

Fruit and seed: Not observed.

Disease and pest resistance: Field observations show tolerance to typical pests of *Rhododendron*, which include lace wings and red mites. The new cultivar did not show susceptibility to root diseases observed in other cultivars in the same field test.

Temperature tolerance: Tolerant to USDA Zone 6.

What is claimed is:

1. A new and distinct cultivar of *Rhododendron* plant named 'ROBLEZO' as herein illustrated and described.

* * * * *